United States Patent [19]

Bashyam

[11] Patent Number: 5,203,869
[45] Date of Patent: Apr. 20, 1993

[54] ULTRASONIC FLANGE RADII INSPECTION TRANSDUCER DEVICE

[75] Inventor: Manohar Bashyam, Mason, Ohio

[73] Assignee: General Electric Company, Cincinnati, Ohio

[21] Appl. No.: 800,909

[22] Filed: Nov. 26, 1991

[51] Int. Cl.⁵ .................... G01N 29/06; G01N 29/24
[52] U.S. Cl. .......................................... 73/640; 73/629
[58] Field of Search .............. 73/627, 629, 632, 633, 73/640, 642, 623

[56] References Cited

U.S. PATENT DOCUMENTS

| | | | |
|---|---|---|---|
| 4,212,207 | 7/1980 | Conradi | 73/623 |
| 4,361,044 | 11/1982 | Kupperman et al. | 73/623 |
| 4,474,064 | 10/1984 | Naruse et al. | 73/622 |
| 4,541,434 | 9/1985 | Okado | 73/633 |
| 4,807,476 | 2/1989 | Cook et al. | 73/620 |
| 4,862,748 | 9/1989 | Woodmansee | 73/641 |

*Primary Examiner*—Tom Noland
*Assistant Examiner*—Rose M. Finley
*Attorney, Agent, or Firm*—Jerome C. Squillaro; Charles L. Moore, Jr.

[57] ABSTRACT

A transducer device for an ultrasonic flaw detection system comprises a right angle rectangular block with one longitudinal edge being shaped to accurately conform to the curvature of the surface to be inspected. An ultrasonic sound wave beam in the block is reflected 90° by a rotating mirror to cut a 360° arc path through the surface to be inspected.

9 Claims, 2 Drawing Sheets

ULTRASONIC FLANGE RADII INSPECTION TRANSDUCER DEVICE

BACKGROUND OF THE INVENTION

This invention relates to an improved ultrasonic flange radii transducer device, and more particularly to an improved transducer holder and mechanism particularly adapted for flange radii flaw detection or evaluation in radii non-metal composite, laminate materials.

Non-metallic materials such as synthetic resins, ceramics, and composite materials containing resins and non-metallic filaments are finding wider applications in rotating machinery components such as hot gas turbine engine components. Many applications include important separate and individual parts manufactured from the noted materials. Composite materials components may be produced by combining layers of the material with a bonding medium and then curing the final product without any or minimal forming pressure or force. As a result the final product may include undesirable voids in the material as well as some delamination. In components having a 90° flange or other corner angle, imposed stresses in the innermost corner of the angle become significantly more critical, particularly if material in the corner region contains flaws such as voids and delaminations. Ordinarily this innermost corner of an angle section includes a raised band or layer of the material with a small radius of curvature surface providing a smooth transition surface between the intersecting or joining surfaces defining the angle or corner. These small radii curve surfaces sometimes referred to as fillets or fillet regions are predetermined in size and shape to counter the high stress concentration usually found where surfaces sharply intersect. Consequently a flaw in the noted innermost corner material or fillet region becomes even more critical as a source or cause of premature failure. Because of the required high degree of precision and quality of hot gas turbine engines and associated components, the noted parts and components with angled surfaces are usually subjected to close and comprehensive inspection, with the result that various testing devices and systems have been developed for their flaw detection. Ultrasonic flaw detection systems have been found favorable for such inspections. In such a system an ultrasound wave is projected perpendicularly into, for example, the surface to be inspected. The sonic wave penetrates the surface and passes through the material of the part being inspected. As the sonic wave passes through the part material, all or part of the wave is reflected by flaws such as inclusions and discontinuities within the material. These reflections are sensed by a transducer and electronically processed to provide a visual and/or recorded interpretation of the flaws. Effectiveness of ultrasonic inspection systems as described is predicated on having a close coupling between the transducer and the inspecting surface, and having the projecting ultrasonic wave enter the surface in perpendicular relationship to maximize wave reflection and detection as well as the characteristics of a discovered flaw. In small radii surfaces such as the small radius interconnecting surface or fillet in the included angle between a pair of angled surfaces, a 90° flange angle, for example, it has been difficult to provide means for continuously projecting an ultrasound beam radially and perpendicularly into the curved surface as well as incrementally and transversely along the curvature of the surface. It also has been a practice to provide sliding or rolling probes or transducers which move along the curved surface in contact relationship to closely follow the curve of as well as to provide close sound coupling with the surface. However, probes adapted to follow and couple with smaller radii curved surfaces represent a continuing problem of wave perpendicularity and close coupling. For this reason various ultrasonic devices and arrangements have been developed to obtain an optimum near perpendicular scan of small flange radii. In general these arrangements continue to include an ultrasound wave emitting transducer probe whether a rubbing probe, or a rotating ball or roller probe, together with appropriate mechanisms which attempt to couple, move, and guide the probe over the surface to be scanned while at the same time retaining a near perpendicular scan. Ultrasound coupling between the curved surface and the contacting probe, as well as obtaining a full and precise scan, together with real time display across the surface remain problem areas.

OBJECTS OF THE INVENTION

It is an object of this invention to provide an improved transducer holder for an ultrasonic defect detection system for small radii surfaces.

It is another object of this invention to provide an improved rotating beam generating transducer holder for an ultrasonic defect detection system for small radii surfaces.

It is a still further object of this invention to provide an improved rotating ultrasonic beam transducer holder for an ultrasonic defect detection system particularly adapted for flange radii inspection.

SUMMARY OF THE INVENTION

A transducer holder for an ultrasonic flaw detection system comprises a single ultrasonic transducer unit which generates and projects an ultrasonic beam into the device in a direction generally parallel to the surface to be inspected. Thereafter, a rotating mirror system in the device reflects the beam through 90° for projection into the surface to be inspected, while rotating the beam through 360° to cut a perpendicular slice through a flange radius. Improved coupling is achieved by having a curved surface of the holder which engages the curved surface to be inspected, be an accurate, corresponding and interfitting curved surface to the curved surface being inspected.

This invention will be better understood when taken in connection with the following drawings and description.

DESCRIPTION OF A PREFERRED EMBODIMENT

Figure 1:
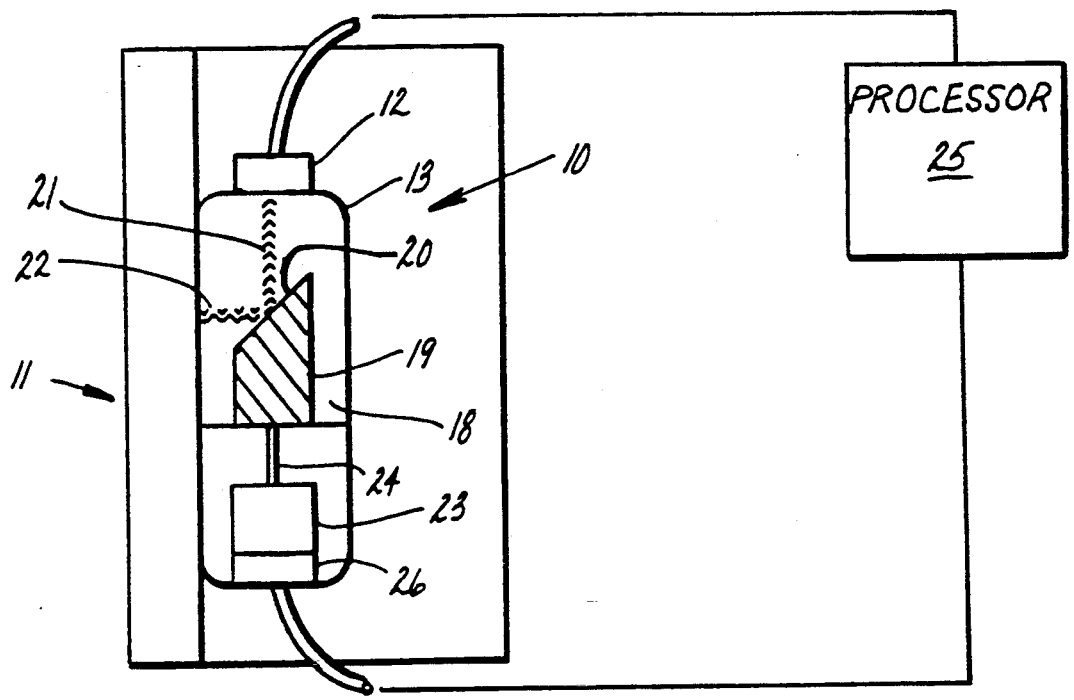
FIG. 1 is a schematic plan view of the transducer holder of this invention in its operative position of inspecting a fillet region of a 90° angle composite material component.

Referring now to FIG. 1, transducer holder 10 of this invention is illustrated in its operative position scanning a 90° angle flange 11. A cylindrical ultrasound transducer 12 is positioned concentrically at one end of a rectangular casing or block 13. Block 13 is an important feature of this invention serving two very important functions of (1) providing a tight sound coupling with the surface to be inspected, and (2) to incorporate components which generate and project a perpendicular sound wave into the surface to be inspected. The material of block 13 must be capable of a tight coupling with flange 11 to provide an uninterrupted and unaltered sound signal from transducer 12 into flange 11. To accomplish this purpose, block 13 must fully and closely match and engage the radius surface to be inspected as illustrated in FIG. 2.

Figure 2:
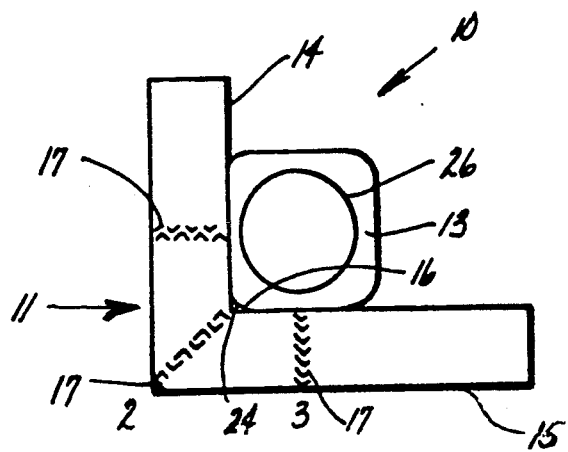
FIG. 2 is schematic and cross-sectional view of the transducer holder of FIG. 1 interfitting in a flange angle.

Referring now to FIG. 2, block 13 is illustrated in close nesting and interfitting relationship in angle 11. Block 13 fits in angle 11 with extensive planar surface to planar surface contact with arms 14 and 15 of angle 11, an arrangement which enhances ultrasound coupling between block 13 and angle 11, as opposed to a ball or roller probe which may only have a very small spot or line contact with arms 14 and 15. A further important feature of rectangular block 13 is the curve of the rounded corner 16 which is the corner fitting innermost in angle 11 and a twin to the small radius surface or fillet in angle 11. The matching curves and accompanying coupling provides increased accuracy of holder 10 as well as an improved pictorial display result of a test. Ordinarily, specifications for fillet regions are known and block 10 may be preformed for the part to be inspected. Block 13 is expeditiously produced from a synthetic resin material such as a polymethyl methacrylate, with commercially available derivations known by their trade names Lucite and Plexiglas. This material is easily shaped for an optimum curvature along the inspecting edge. Ultrasonic transducer 12 produces an ultrasonic sound wave which is Projected into block 13 and reflected to project into angle 11 as an arc traversing beam 17 in a specific manner as illustrated in FIG. 1.

Referring again to FIG. 1, which is a schematic and longitudinal view of transducer holder 10 of FIG. 2, resin block 13 includes a hollow chamber or section 18 which contains a metal wedge reflector member 19. In one example wedge reflector member 19 is a cylindrical rod of stainless steel with a highly polished mirror surface 20 angled at 45° with respect to the longitudinal axis of block 13 and sound beam 21 from transducer 12. Ultrasound transducer 12 and wedge member 19 are positioned and arranged so that ultrasound beam 21 is axially projected directly to mirror 20 and reflected through 90° to penetrate angle 11 as beam 22. In order for beam 22 to scan the total radius to be inspected, beam 22 is provided with means for arc rotation. A small D.C. motor drive 23 is contained in an end section of block 13 opposite transducer 12, and wedge member 19 is mounted for coaxial rotation by shaft 24 of motor drive 23. Sound wave 22 is thereby caused to traverse a full 360° by rotation of wedge member 19 and the full 90° angle of angle 11 is traversed in a close precise manner by the rotating beam 22 in a thin 360° arc. The ultrasonic scanning beam provides a full 90° scan of an angle as shown in FIG. 2 by the three inner position segments 17 of the beam penetrating perpendicularly into each surface being inspected while progressing across the 90° arc.

Ultrasound coupling is significantly enhanced by hollow chamber 18 being fluid filled with a good ultrasound transmitting fluid, for example, water. Water in chamber 18 may be referred to as an isolated water filled chamber, i.e. not connected to a water source or discharge for replenishment or flow. The capability of this invention to function with an isolated water filled chamber 18 contributes favorably to its manipulativeness and portability. The transmitted sound signal 22 enters the small radius surface in angle 11 accurately and perpendicularly along its radial arcuate path and is reflected by any anomaly between front and back surfaces. By monitoring those reflections, anomalies in the material are non-destructively detected. Monitoring usually includes sensing sonic wave reflections by the transducer and processing the reflections electronically for a visual display. In FIG. 1 electronic processing means are generally shown as box 25 appropriately electrically connected to transducer holder 10. Electronic systems for processing such reflected signals are noted in U.S. Pat. No. 4,807,476—Cook et al and may be included in processor 25 which also serves as a source of electrical power for holder 10 and its components. The foregoing procedure provides an extremely accurate but limited inspection of the small radius surface at one very limited position or cross-section. In order to obtain this kind of inspection transversely along the radius, transducer holder 10 is caused to move or index transversely while the 360° scanning is occurring. Transverse movement is correlated with mirror 20 rotation so that, for example, one increment of transverse movement occurs for each 360° revolution of wedge member 19 and mirror 20. Further, a visual display in the usual manner on a CRT occurs for the cross-section inspected, and an optical encoder 26 (FIG. 1) is interconnected in the system to provide an operator or computer the positional feedback in degrees of angle, of wedge 19 and mirror 20 rotation. One example of an inspection of an angle 11 is illustrated in FIG. 3.

Figure 3:
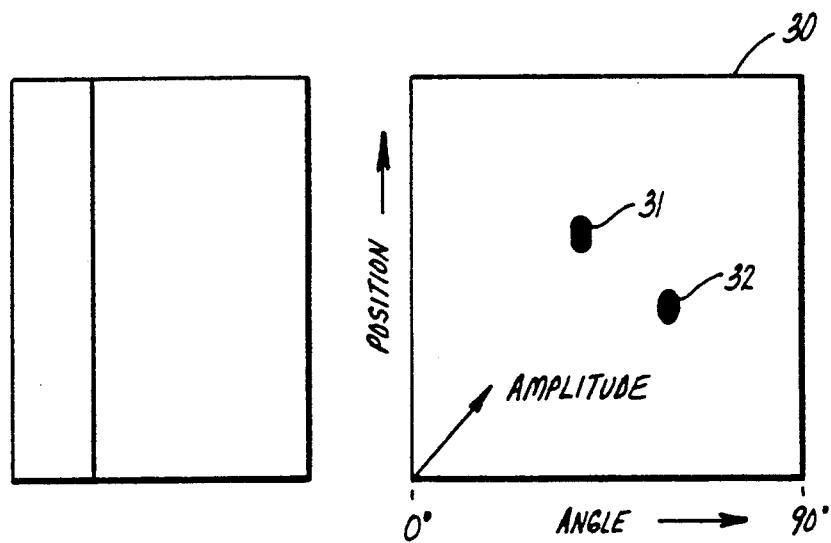
FIG. 3 is a pictorial illustration obtained by electronically processing reflected ultrasound signals from a practice of this invention, which is knows as a C scan.
Figure 4:
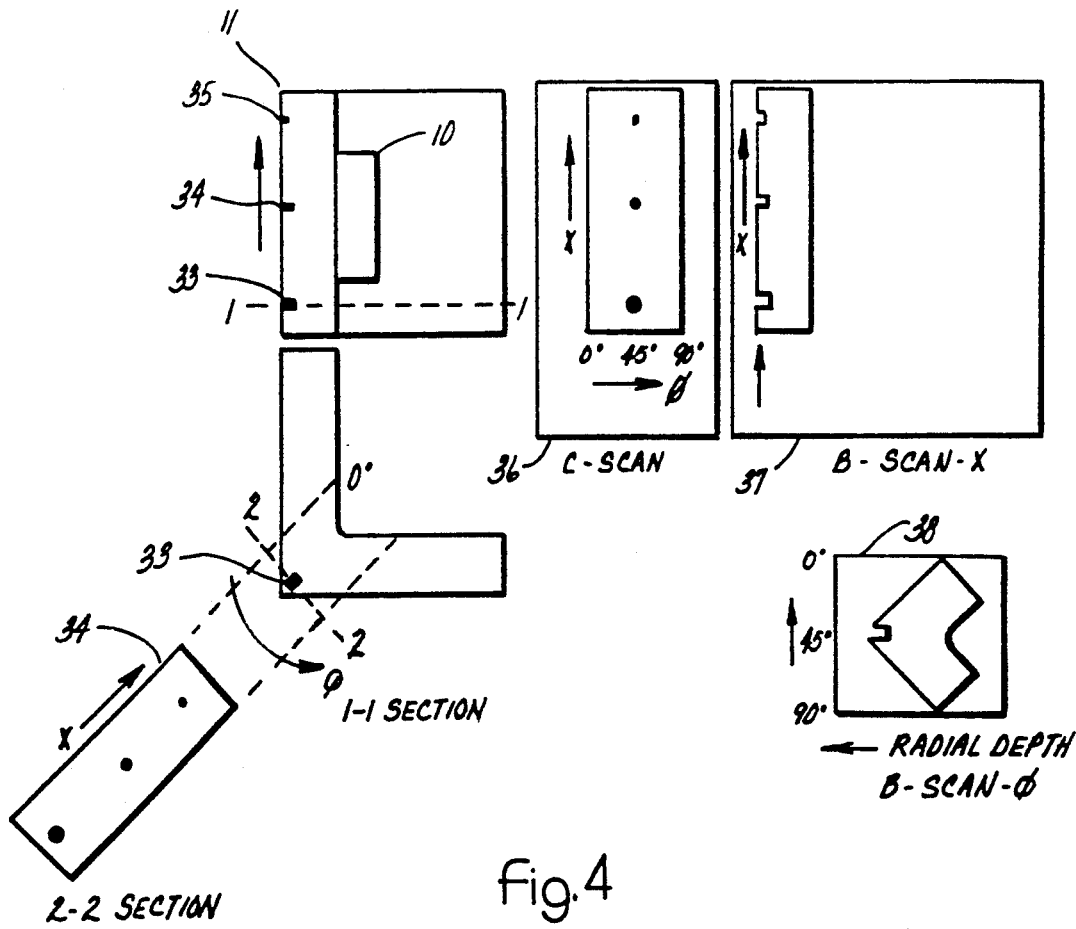
FIG. 4 is a C scan and B scan illustration obtained from electronic processing of reflected ultrasound signals from a practice of this invention.

Referring now to FIG. 3, visual plot 30 shows a pair of representative defects 31 and 32 in angle 11 of FIG. 1 as a C scan display. In order to obtain a faster scan of the small radius surface, a B-scan (brightness mode display) of the inspected surface is displayed for each cross-section inspected. To do this in real time, wedge member 19, and its mirror 20, is rotated at at least about 30 revolutions per second, 30 RPS, and transducer device 10 is caused to correspondingly slowly move transversely. This correlated movement together with a scanning display for each inspected cross-section (obtained by matched radii of the transducer holder 10 and the surface to be inspected) provides an improved ultrasound flaw inspection for various small radii surfaces in included angle regions, particularly enhanced by a 360° perpendicular sweep of sound beam 22, and providing real time viewing of internal flaws. FIG. 4 of this invention includes an example of a T.V. monitor or CRT display of a C scan display as well as a concurrent and faster B-scan a described.

FIG. 4 is an operational view of a practice of this invention in combination with visual scan results. In an appropriate test procedure for FIG. 4, angle 11 was provided with certain programmed and predetermined hidden flaws or defects to be detected and visually displayed. For example, a series of flat bottom holes or apertures 33–35 were drilled angularly into the heel of angle 11 and in a row transversely along angle 11 as illustrated in the 1—1 section of FIG. 4. Transducer assembly 10 of this invention is shown in its operative position in angle 11 and is moved transversely to scan along the small radius inner surface of the 90° angle 11. With appropriate electronic circuitry as described, a CRT C scan 36 is presented and shows that the programmed defects 33–35 have been detected as well as angularly located. With coordinated mirror rotation (FIG. 1) and transverse movement of assembly 10, a B scan 37 is displayed. As illustrated in FIG. 4, B scan 37 provides an indication of the depth of defects 33–35.

FIG. 4 is indicative of the essential difference between C scans and B scans. A C scan is a distance vs. distance or angle presentation while a B scan is a distance vs. depth or angle vs. depth presentation. A B scan can be compared to a scanned cross-section at a given plane along the angle 11 which may be referred to in FIG. 4 as B scan X at an angle, for example, of 45°. The cross-section for B scan O, presentation 38, of FIG. 4 is a given position X along angle 11 and at 0°–90° angle. A C scan is a projection or plan view of the scanned area.

This invention provides an improved transducer holder with a synthetic resin block or head having a curved surface which precisely fits coincident with the innermost part of an angle structure such as a 90° flange structure for a precise and accurate flaw inspection of the specific matched angle surface. The 360° sonic wave sweep provides a wide range of inspection for angles less than and more than 90°. Accuracy of this invention requires a careful match between the contacting curvature of transducer and the curvature of the part to be inspected as well as an intervening material, i.e. block 13 as the holder contacting surface, which is effective to propagate a sound wave from an ultrasonic transducer into the surface to be inspected.

By means of the improved single ultrasonic transducer of this invention, a more precise scan is obtainable on a known small radius of a flanged part or component. The improved transducer includes more precise coupling between the radius to be scanned and the transducer together with a larger angle faster scan with a real time visual display.

While this invention has been described with respect to a preferred embodiment, it will be understood by those skilled in the art that various changes and modifications may be made without departing from the spirit and scope of the invention of the following claims.

What is claimed:

1. An improved ultrasonic transducer holder for ultrasonic inspection of internal flaws in a material in a predetermined small radius of curvature surface at the intersection of a pair of surfaces comprising in combination
   (a) a generally rectangular block member of a synthetic resin material,
   (b) at least one continuous longitudinal edge of said block member having a radius of curvature matching the predetermined small radius of curvature surface for precise fitting contact between said at least one longitudinal edge and said small radius of curvature surface,
   (c) an ultrasonic sound transducer positioned at one end of said block member and adapted to provide an ultrasonic sound beam in said block member,
   (d) mirror means in said block member to reflect said beam 90° from said beam's original direction through said material of said at least one longitudinal edge and into said small radius of curvature surface,
   (e) electric motor drive means to rotate said mirror means to cause said reflected beam to traverse an arc path of 360° while being projected perpendicularly into said small radius of curvature surface.

2. The invention as recited in claim 1 wherein said mirror means comprises a rotating ultrasound beam reflecting mirror mounted at a 45° angle to the original direction of said beam from said transducer.

3. The invention as recited in claim 1 wherein said mirror means is submerged in an isolated fluid filled chamber in said block member.

4. The invention as recited in claim 1 wherein said small radius of curvature surface is an inner radius fillet surface at an intersection of two right angle surfaces into which said block interfits.

5. The invention as recited in claim 4 wherein said rectangular block member interfits in said intersection in a full angle planar surface to planar surface contact.

6. The invention as recited in claim 1 wherein said material in said small radius of curvature surface is a composite non-metal material.

7. An improved ultrasonic transducer holder for ultrasonic flaw detection systems adapted to detect flaws in a material in a small radius of curvature surface between a pair of intersecting surfaces comprising in combination
   (a) a right angular rectangular block of a synthetic resin material,
   (b) said block having a hollow chamber therein adjacent one end and at least one continuous longitudinal edge of said block member having a radius of curvature matching the small radius of curvature surface for fitted contact therewith,
   (c) an electrical ultrasonic signal generating means at one end of said hollow chamber to generate an ultrasonic sound beam passing into said chamber longitudinally therein with respect to said block,
   (d) an ultrasonic beam mirror mounted in said chamber opposite said ultrasonic signal generating means at a 45° angle with respect to said ultrasonic sound beam to reflect said beam 90° in a direction through said at least one longitudinal edge and into said small radius of curvature surface,
   (e) electric motor drive means in said block to rotate said mirror such that said reflected ultrasonic beam traverses a 360° circle of rotation through said small radius of curvature surface,
   (f) electronic means associated with said block to generate a visual display of reflections of said beam from flaws in the material of said small radius of curvature surface.

8. The invention as recited in claim 7 wherein an optical encoder is connected to said electric motor drive means and said mirror to provide an angular location of flaws in said visual display.

9. The invention as recited in claim 7 wherein said hollow chamber is an isolated fluid filled chamber.

* * * * *